(12) United States Patent
Chung et al.

(10) Patent No.: US 8,942,815 B2
(45) Date of Patent: Jan. 27, 2015

(54) ENHANCING COCHLEAR IMPLANTS WITH HEARING AID SIGNAL PROCESSING TECHNOLOGIES

(76) Inventors: King Chung, West Lafayette, IN (US); Fan-Gang Zeng, Irvine, CA (US)

(\*) Notice: Subject to any disclaimer, the term of this patent is extended or adjusted under 35 U.S.C. 154(b) by 1072 days.

(21) Appl. No.: 10/805,016

(22) Filed: Mar. 19, 2004

(65) Prior Publication Data

US 2005/0209657 A1   Sep. 22, 2005

(51) Int. Cl.
*A61N 1/00* (2006.01)
*A61N 1/36* (2006.01)

(52) U.S. Cl.
CPC .................................. *A61N 1/36032* (2013.01)
USPC .......................................................... 607/57

(58) Field of Classification Search
USPC .............................. 607/55–57, 137
See application file for complete search history.

(56) References Cited

U.S. PATENT DOCUMENTS

| | | | | |
|---|---|---|---|---|
| 4,467,145 A * | 8/1984 | Borstel | ......................... | 381/329 |
| 4,593,696 A * | 6/1986 | Hochmair et al. | .............. | 607/57 |
| 5,479,522 A * | 12/1995 | Lindemann et al. | ......... | 381/23.1 |
| 5,524,056 A * | 6/1996 | Killion et al. | .................. | 381/314 |
| 5,531,774 A * | 7/1996 | Schulman et al. | ............... | 607/56 |
| 5,824,022 A * | 10/1998 | Zilberman et al. | .............. | 607/57 |
| 6,195,585 B1 * | 2/2001 | Karunasiri et al. | .............. | 607/57 |
| 6,212,431 B1 * | 4/2001 | Hahn et al. | ....................... | 607/61 |
| 6,394,947 B1 * | 5/2002 | Leysieffer | ........................ | 600/25 |
| 6,620,094 B2 * | 9/2003 | Miller | .............................. | 600/25 |
| 6,839,447 B2 * | 1/2005 | Nielsen et al. | ................. | 381/312 |
| 6,862,359 B2 * | 3/2005 | Nordqvist et al. | ............. | 381/312 |

\* cited by examiner

*Primary Examiner* — Mark W Bockelman
(74) *Attorney, Agent, or Firm* — McAndrews, Held & Malloy, Ltd.

(57) ABSTRACT

A system and method that enhance the performance of cochlear implant signal processing in an amplification device. The system utilizes a signal input device that picks up the sounds from the environment or other hearing or audio devices and feeds the incoming signal into a front-end signal processor. The front-end processor pre-processes the signals and feeds them into a cochlear implant signal processor. The system may also insert a front-end processor into multiple signal processing stages of a cochlear implant signal processor with the front-end processor "sandwiched" between the multiple signal processing stages of the cochlear implant signal processors. The system may also insert a front-end processor into multiple signal processing stages of a cochlear implant signal processor with the front-end processor being either an integrated part of the cochlear implant signal processor or a functionally distinctive part for bilateral cochlear implants.

5 Claims, 15 Drawing Sheets

ENHANCING COCHLEAR IMPLANTS WITH HEARING AID SIGNAL PROCESSING TECHNOLOGIES

RELATED APPLICATIONS

[Not Applicable]

FEDERALLY SPONSORED RESEARCH OR DEVELOPMENT

[Not Applicable]

MICROFICHE/COPYRIGHT REFERENCE

[Not Applicable]

BACKGROUND OF THE INVENTION

A hearing aid generally refers to an amplification device, which may have a microphone to pick up sounds from the environment surrounding the person wearing the hearing aid or a direct audio input that receives electrical signal from another device, a signal processor to process the sounds, and a receiver to transmit acoustic energy to the user's ear canal or to a coupling device then to the user's ear canal (as in acoustic hearing aids). The receiver may be replaced by a bone vibrator to transmit mechanical energy to the temporal bone (as in bone-conduction hearing aids). The signal processor's processing of the sounds depends on the user's hearing loss and the nature of the sounds.

A cochlear implant generally refers to a device that has a microphone to pick up sounds from the environment or a direct audio input that receives electrical signal from another device, a speech processor to process the sounds and covert them to electric pulses using different speech coding strategies (e.g., CIS, SPEAK, SAS, HiRes), a transmitter to send the pulses across the skull, and a receiver/stimulator to send the pulses to an electrode array implanted in the cochlea to stimulate auditory nerves. FIG. 1 illustrates a block diagram of an exemplary cochlear implant system.

In the past decade, technologies for hearing aids have advanced significantly. For example, many hearing aids have directional microphones and adaptive directionality algorithms to reduce noise interference; some hearing aids have microphone-matching algorithms to maintain the directional performance of the hearing aids; and some hearing aids may also have an automatic-switching mechanism for telecoil-microphone modes, for directional-omni-directional modes, and for different listening programs. These technologies have allowed hearing aid users to have better speech understanding, more listening comfort, and added convenience.

Difficulties in understanding speech in noise have been the most frequent complaints from both hearing aid and cochlear implant users. Research has shown that hearing aid and cochlear implant users have more difficulties in understanding speech in noisy environments than people with normal hearing, depending on the spectral and temporal characteristics of the background noise (Dirks, Morgan & Dubno, 1982; Dorman et al, 1998; Duquesnoy, 1983; Eisenberg, Dirks & Bell, 1995; Festen & Plomp, 1990; Gengel, 1971; Kessler et al., 1997; Plomp, 1994; Skinner et al., 1994; Soede, 2000, Peters, Moore & Baer, 1998, Tillman, Carhart & Olsen, 1970; Zeng & Galvin, 1999). Noise creates difficulties in speech understanding, which may elicit other negative reactions for hearing aid users, such as, annoyance, headaches, fatigue, embarrassment, and social isolation.

From a signal processing point of view, the differences between speech and noise may be explored by their temporal, spectral, and/or spatial characteristics and relationships. Temporally, noise may co-exist with targeted speech at the same instance or they may occur at different instances. Spectrally, the frequency spectrum of speech and noise may overlap or occur at different frequency regions. Spatially, noise may originate from a different spatial angle than the targeted speech, or noise may come from the same direction as the targeted speech.

Multiple technologies have been developed to reduce the detrimental effect of background noise on hearing aids, such as noise reduction/speech enhancement algorithms, directional microphones, microphone matching algorithms, and adaptive directionality algorithms. Speech enhancement algorithms exaggerate the spectral and/or temporal contrast in an attempt to enhance speech intelligibility (Olsen, 2002; Matsui & Lemons, 2001). Noise reduction algorithms are mainly designed to reduce noise interferences. Some noise reduction algorithms take advantage of the spectral separation between speech and noise and some noise reduction algorithms take advantage of the temporal separation between speech and noise. Algorithms that take advantage of the spectral separation between speech and noise detect the frequency bands with speech-like signal dominance or with noise-like signal dominance, and reduce the gain of the frequency bands at which noise occurs (Kuk, Ludvigsen & Paludan-Muller, 2002; Johns, Bray & Nilsson, 2001; Olsen, 2002). Other algorithms attempt to take advantage of the temporal separation between speech and noise. When no speech is detected, the algorithm gradually reduces the gain or increase compression of the hearing aid. When speech is present, the algorithm instantaneously restores the gain to the normal settings (Bachler, Knecht, Launer & Uvacek, 1997; Elberling, 2002). Some of the noise-reduction algorithms are proven to either enhance speech understanding or increase listening comfort for hearing aid users (Bray & Nilson, 2001; Bray & Valente, 2001, Chung, 2002, Chung, 2003).

While noise reduction algorithms take advantage of temporal and spectral separations between speech and noise, directional microphones have reportedly been more effective in reducing background noise originating from different spatial locations than the targeted speech, for both hearing aid and cochlear implant users (Cord et al., 2002; Hawkins & Yacullo, 1984; Killion et al., 1997; Ricketts et al., 2001; Wouters & Vanden Berghe, 2001, Wouters et al., 2002). Many hearing aid manufacturers have also implemented various advanced algorithms to make directional microphones more effective. These advanced algorithms include adaptive directionality algorithms to detect the location of noise and change the polar pattern of the directional microphone system so that noise is maximally reduced. This feature may be especially useful if the relative location of speech and noise changes in space (Ricketts & Henry, 2002). Other such advanced algorithms include in-situ microphone matching algorithms to match the frequency response of the microphones when the hearing aid is worn in the ear in order to compensate for microphone drift and to obtain maximum directional performance. Although some cochlear implant systems may offer directional microphone technology, few cochlear implant manufacturers have implemented these advanced algorithms in their products.

In addition, many hearing aid manufacturers have developed automatic switches for switching between directional and omni-directional modes, among different listening programs and switchless telecoils. Directional microphones are generally used in noisy environments to reduce noise interference, while omni-directional microphones are generally preferable in quiet environments or when there is wind noise. Usually, the switch between the two modes is accomplished manually. Automatic switch algorithms for different microphone modes can automatically turn the hearing aids to directional mode in noisy environments and to omni-directional mode in quiet environments. For example, when a hearing aid user walks from a quite room to a noisy party, the hearing aids would automatically switch from omni-directional mode to directional mode. When the person walks away from the crowd, the hearing aid would automatically switch back to omni-directional mode. Similarly, the automatic switch algorithms for different listening program can detect the characteristics of incoming sounds, make inferences of the environment that the user is in, and automatically switch to appropriate listening program for the user. In addition, switchless telecoils can automatically switch to telecoil mode when a magnetic field is detected (i.e., when a telephone headset is positioned near the ear), and automatically switch back to microphone mode when the magnetic field disappears (i.e., when the telephone headset is moved away from the ear). Automatic switches can reduce time delays associated with manually switching between the different modes. Automatic switches also offer considerable convenience for hearing aid users, especially for older users whose fingers may not be as sensitive as younger users. These advanced options are not available for cochlear implant users.

FIG. 1 illustrates a block diagram of an exemplary cochlear implant system.

Further limitations and disadvantages of conventional and traditional approaches will become apparent to one of ordinary skill in the art through comparison of such systems with the present invention.

BRIEF SUMMARY OF THE INVENTION

Aspects of the present invention may be seen in a system that enhances the performance of cochlear implants. The system comprises a first processor that processes signals in hearing aids or other audio devices; a second processor that processes and encodes signals in the cochlear implants; and at least one microphone.

In an embodiment of the present invention, the first processor and the at least one microphone may be added to the second processor. The first processor and the at least one microphone may be housed in an in-the-ear case, while the second processor may be housed in a behind-the-ear case or a body-worn case.

In an embodiment of the present invention, the first processor and the at least one microphone may be integrated with the second processor. The first processor, the at least one microphone, and the second processor may be housed in a behind-the-ear case. The first processor and the at least one microphone may be housed in a behind-the-ear case, while the second processor may be housed in a body-worn case. The at least one microphone may be housed in a behind-the-ear case, while the first processor and the second processor may be housed in a body-worn case. This embodiment may comprise a circuit that provides compatibility matching between the first processor and the second processor.

In an embodiment of the present invention, the processing in the first processor and/or the second processor may comprise at least one of: multiple signal processing stages; multiple signal processing algorithms; and multiple components. The first processor may also contain multiple signal feeding points and multiple signal extraction points to which connection can be made to feed signals into and extract signal from the system.

In an embodiment of the present invention, the first processor may be inserted between multiple signal processing stages of the second processor.

A method that enhances the performance of cochlear implant speech processing in an amplification device, comprises collecting signals in the environment by the at least one microphone; preprocessing the collected signals in the first processor; feeding the preprocessed signal into the second processor; processing the signal in the second processor; and feeding the processed signal into a transmitter.

These and other features and advantages of the present invention may be appreciated from a review of the following detailed description of the present invention, along with the accompanying figures in which like reference numerals refer to like parts throughout.

DETAILED DESCRIPTION OF THE INVENTION

Aspects of the present invention relate generally to the field of cochlear implant design, and more particularly to the improvement of cochlear implant speech processing for enhancing speech understanding, listening comfort, perceived sound quality and convenience of cochlear implant usage.

In an embodiment of the present invention, a cochlear implant module containing a signal processor may be enhanced using a front-end processor. The front-end processor may be a signal processor such as, for example, a hearing aid signal processor or a hearing protector signal processor. The front-end processor may enhance the performance of the cochlear implant by adding such capabilities as, for example, directional microphones, adaptive directionality algorithms, noise reduction algorithms, switchless telecoils, wireless programming capabilities, etc.

In an embodiment of the present invention, the connections to and from the front-end signal processor and the cochlear implant signal processor may be in analog or digital format.

In an embodiment of the present invention, the front-end processor and/or the cochlear implant signal processor may perform the signal processing. The signal processing may be done using hardware, software, or a combination thereof.

In an embodiment of the present invention, a compatibility matching circuit/algorithm may be added at the interface of the front-end processor and the cochlear implant signal processor to minimize distortion and to eliminate any possible incompatibility such as, for example, signal format, signal scaling, impedance mismatch, etc., between the hearing aid signal processor and the cochlear implant signal processor.

Figure 1:
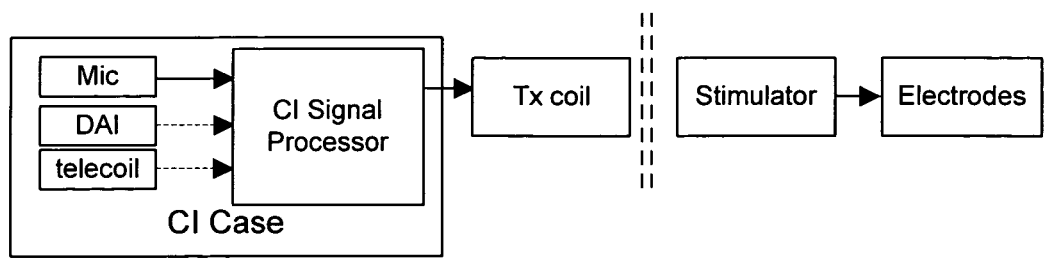
FIG. 1 illustrates a block diagram of an exemplary cochlear implant system.
Figure 2A:
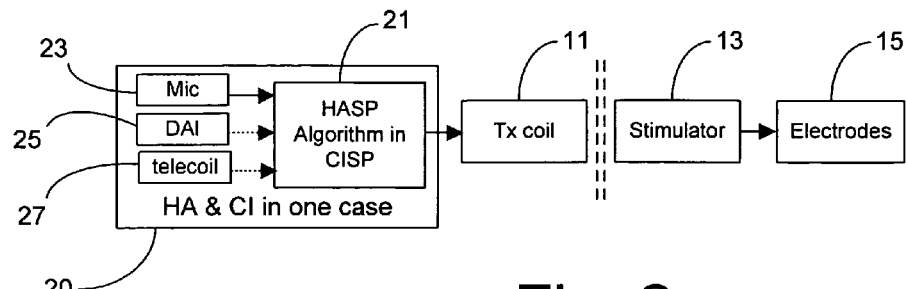
FIG. 2a illustrates a block diagram of an exemplary enhanced cochlear implant system, in accordance with an embodiment of the present invention.

FIG. 2a illustrates a block diagram of an exemplary enhanced cochlear implant system, in accordance with an embodiment of the present invention. In this system a case 20 contains a microphone 23, a direct audio input 25, a telecoil input 27, and a cochlear implant signal processor 21. The signal processor 21 may be enhanced by adding signal processing algorithms such as, for example, algorithms used in hearing aids. The microphone 23, the direct audio input 25, or the input telecoil 27 may pick up the audio signal and send it to the cochlear implant signal processor 21. The hearing aid signal processing algorithms may process the incoming signal first and then send the signal to the cochlear implant signal processor 21, which processes and encodes the signal. The cochlear implant signal processor 21 then sends the signal to the implanted stimulator 13, via the transmitter 11. The stimulator 13 may then stimulate the electrodes 15 implanted in the cochlea.

Figure 2B:
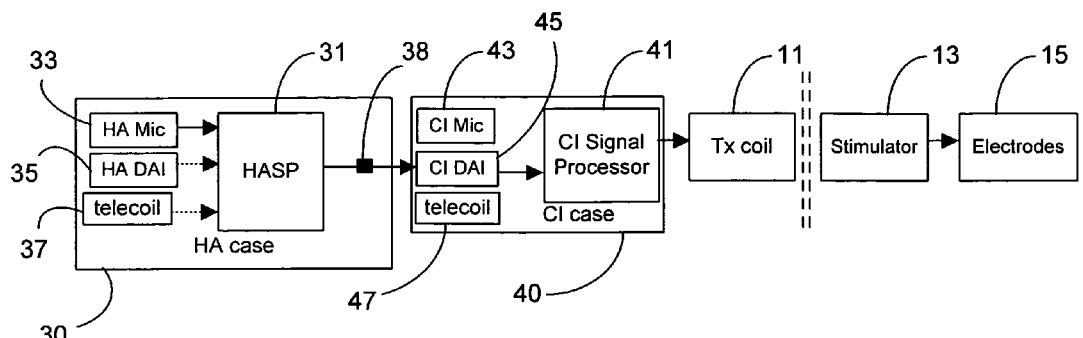
FIG. 2b illustrates a block diagram of another exemplary enhanced cochlear implant system, in accordance with an embodiment of the present invention.

In an embodiment of the present invention, the algorithms of the front-end processor may be implemented on the chip, which may also contain the algorithms of the cochlear implant signal processor. In such an embodiment, the algorithms of the front-end processor may perform some initial processing on incoming signals picked up by the microphones, then send the processed signals to the cochlear implant signal processor of the cochlear implant system for further processing FIG. 2b illustrates a block diagram of an exemplary enhanced cochlear implant system, in accordance with an embodiment of the present invention. In an embodiment of the present invention, the front-end processor 31 such as, for example, a hearing aid or a hearing protector signal processor may be externally added to an existing cochlear implant system. In such an embodiment, an external case 30 containing a microphone 33, a telecoil 37, and a direct audio input 35 compatible with the signal processor 31, a hearing aid signal processor 31, and a compatibility matching circuit 38 may be added to a cochlear implant system contained in a cochlear implant case 40. The cochlear implant case 40 may contain a signal processor 41, a microphone 43, a telecoil 47, and a direct audio input 45. In such an embodiment, the microphone 33, the telecoil 37, or the direct audio input 35 may capture a sound, which may then be processed in the signal processor 31. The processed signal may then be fed into the cochlear implant system via the direct audio input 45 or telecoil 47. The signal processor 41 may then process and encode the signal and send it to the implanted stimulator 13, via the transmitter 11. The stimulator 13 may then stimulate the electrodes 15 implanted in the cochlea.

In an embodiment of the present invention, the front-end processor may be connected to the cochlear implant system using a wire, or a wireless connection. In such an embodiment, the front-end processor may perform some initial processing on incoming signals picked up by the microphones, then send the processed signals to the cochlear implant signal processor of the cochlear implant system for further processing.

Figure 2C:
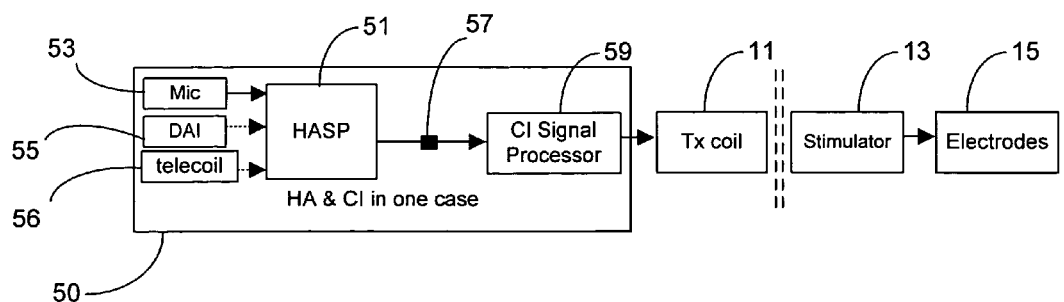
FIG. 2c illustrates a block diagram of another exemplary enhanced cochlear implant system, in accordance with an embodiment of the present invention.

FIG. 2c illustrates a block diagram of another exemplary enhanced cochlear implant system, in accordance with an embodiment of the present invention. In an embodiment of the present invention, the front-end processor 51 such as, for example, a hearing aid or hearing protector signal processor may be integrated into an existing cochlear implant system. In such an embodiment, a case 50 may contain a signal processor 51, a microphone 53, a direct audio input 55, a telecoil 56, and a cochlear implant signal processor 59. In such an embodiment, the microphone 53, the telecoil 56, or the direct audio input 55 may capture a sound, which may then be processed in the signal processor 51. The processed signal may then be fed into the cochlear implant signal processor 59, which may then process and encode the signal and send it to the implanted stimulator 13, via the transmitter 11. The stimulator 13 may then stimulate the electrodes 15 implanted in the cochlea. In an embodiment of the present invention, the case 50 may also contain a compatibility matching circuit 57 between the hearing aid signal processor 51 and the cochlear implant signal processor 59.

In an embodiment of the present invention, the front-end processor may be integrated into a cochlear implant case. In such an embodiment, the front-end processor may perform some initial processing on incoming sounds and signals picked up by the microphones, the telecoil, or the direct audio input then send the processed signals to the signal processor of the cochlear implant system for further processing.

Figure 2D:
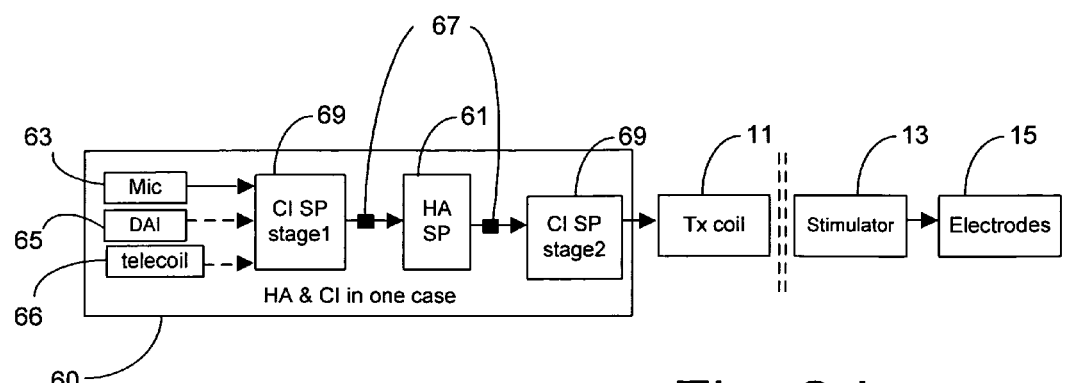
FIG. 2d illustrates a block diagram of another exemplary enhanced cochlear implant system, in accordance with an embodiment of the present invention.

FIG. 2d illustrates a block diagram of another exemplary enhanced cochlear implant system, in accordance with an embodiment of the present invention. In an embodiment of the present invention, the front-end processor 61 such as, for example, a hearing aid or hearing protector signal processor may be integrated into an existing cochlear implant system. In such an embodiment, a case 60 may contain a signal processor 61, a microphone 63, a telecoil 66, a direct audio input 65, and a cochlear implant signal processor 69. In such an embodiment, the microphone 63, the direct audio input 65, or the telecoil 66 may capture a sound, which may be processed by stage 1 of the cochlear implant signal processor 69. The processed signal may then be processed in the signal processor 61 and fed into stage 2 of the cochlear implant signal processor 69, which may then process the signal and send it to the implanted stimulator 13, via the transmitter 11. The stimulator 13 may then stimulate the electrodes 15 implanted in the cochlea. In an embodiment of the present invention, the case 60 may also contain a compatibility matching circuit 67 between stage 1 of the cochlear implant signal processor 69 and the signal processor 61, and between the signal processor 61 and stage 2 of the cochlear implant signal processor 69.

In an embodiment of the present invention, the front-end processor may be integrated into a cochlear implant system, wherein some initial processing may be performed by the cochlear implant signal processor. The front-end processor may then perform some more processing on the results of the initial processing or as part of the initial processing, and the cochlear implant signal processor may complete the processing.

Figure 2E:
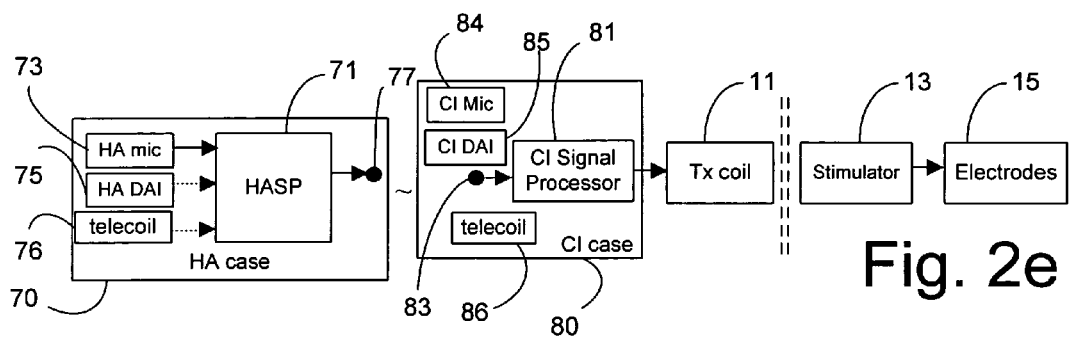
FIG. 2e illustrates a block diagram of another exemplary enhanced cochlear implant system, in accordance with an embodiment of the present invention.

FIG. 2e illustrates a block diagram of another exemplary enhanced cochlear implant system, in accordance with an embodiment of the present invention. In an embodiment of the present invention, the front-end processor 71 such as, for example, a hearing aid or hearing protector signal processor may be externally added to an existing cochlear implant system. In such an embodiment, an external case 70 containing a signal processor 71, a microphone 73, a telecoil 76, or a direct audio input 75 compatible with the signal processor 71, and a wireless transmitter 77. A wireless receiver 83 may be added to a cochlear implant system contained in a cochlear implant case 80. The cochlear implant case 80 may contain a microphone 84, direct audio input 85, and telecoil 86 compatible with the cochlear implant signal processor 81, and a cochlear implant signal processor 81. In such an embodiment, the microphone 73, the direct audio input 75 or the telecoil 76 may capture a sound, which may then be processed in the signal processor 71. The processed signal may then be wirelessly transmitted to the cochlear implant system via the wireless transmitter 77 and received by the wireless receiver 83. The cochlear implant signal processor 81 may then process the signal and send it to the implanted stimulator 13, via the transmitter 11. The stimulator 13 may then stimulate the electrodes 15 implanted in the cochlea.

In an embodiment of the present invention, the hearing aid or hearing protector signal processor 71 may transmit the processed signal via the wireless transmitter 77. The cochlear implant signal processor 81 may then receive the pre-processed signal via a wireless receiver 83 and complete the processing of the signal.

In an embodiment of the present invention, the hearing aid signal processor may output a processed signal as an acoustic output into a cavity such as, for example, the ear canal. In such an embodiment, a microphone may be connected to the signal processor of the cochlear implant. The microphone may pick up the pre-processed acoustic output and feed it into the signal processor of the cochlear implant for further processing.

Figure 3A:
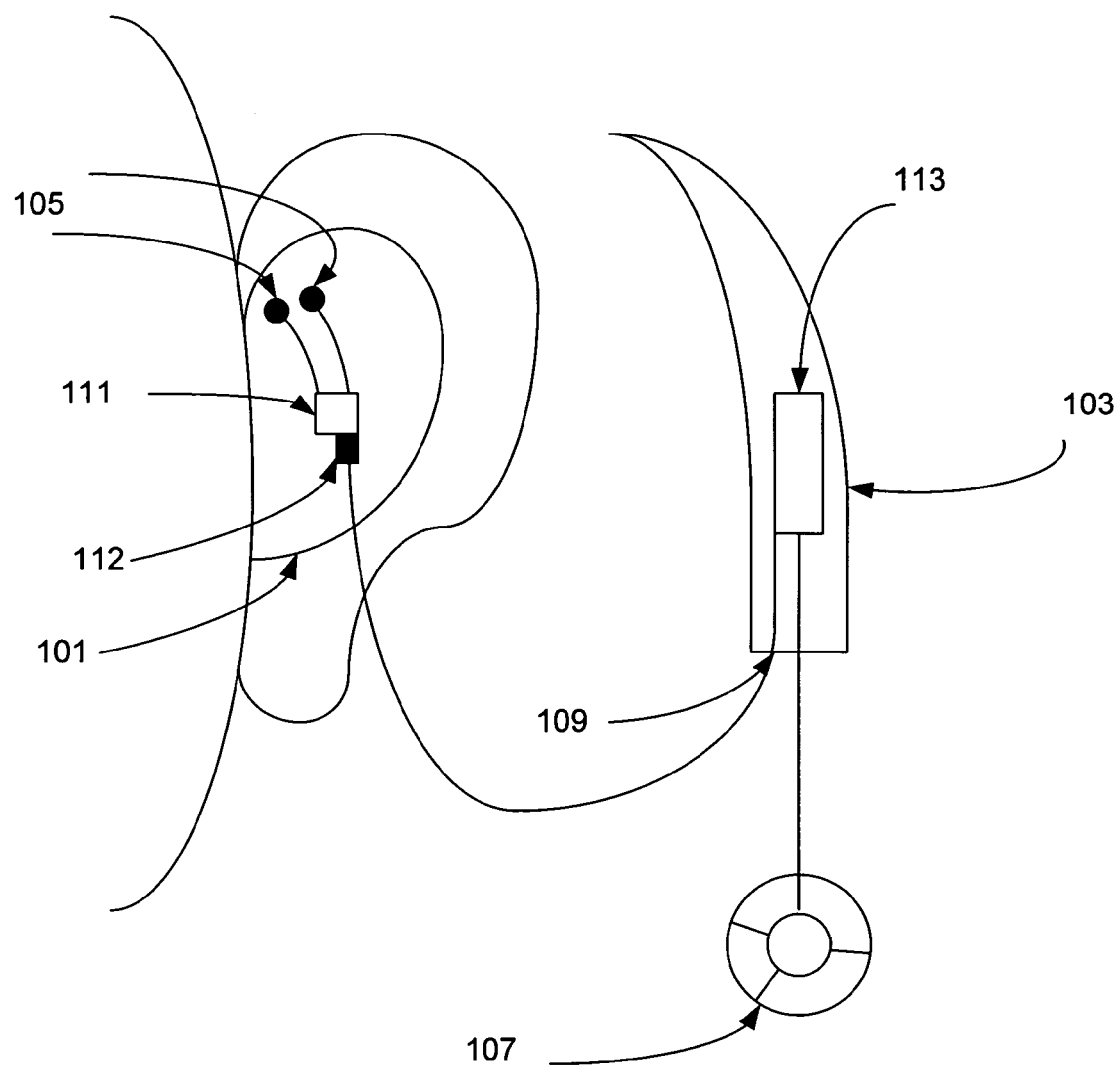
FIG. 3a illustrates an exemplary method of adding an external component that houses a front-end signal processor, to a cochlear implant speech processor, in accordance with an embodiment of the present invention.

FIG. 3a illustrates an exemplary method of adding an external component that houses the front-end signal processor, to a cochlear implant signal processor, in accordance with an embodiment of the present invention. In an embodiment of the present invention, a signal input device 105 such as, for example, microphone(s), direct audio input, or telecoil, along with the a hearing aid signal processor 111 and a compatibility matching circuit 112, housed in an in-the-ear hearing aid case 101, may be added to a cochlear implant system with a cochlear implant signal processor 113. The cochlear implant signal processor 113 may be housed in a behind-the-ear case 103. The pre-processed signal may be transmitted to the cochlear implant signal processor 113 via a direct audio input 109.

In an embodiment of the present invention, the system may utilize an in-the-ear hearing aid case 101 to house the signal input device 105, and the hearing aid signal processor 111. The signal pre-processed by the hearing aid signal processor 111 may be fed into the cochlear implant signal processor 113 via a direct audio input/digital input 109 of the cochlear implant signal processor 113.

Figure 3B:
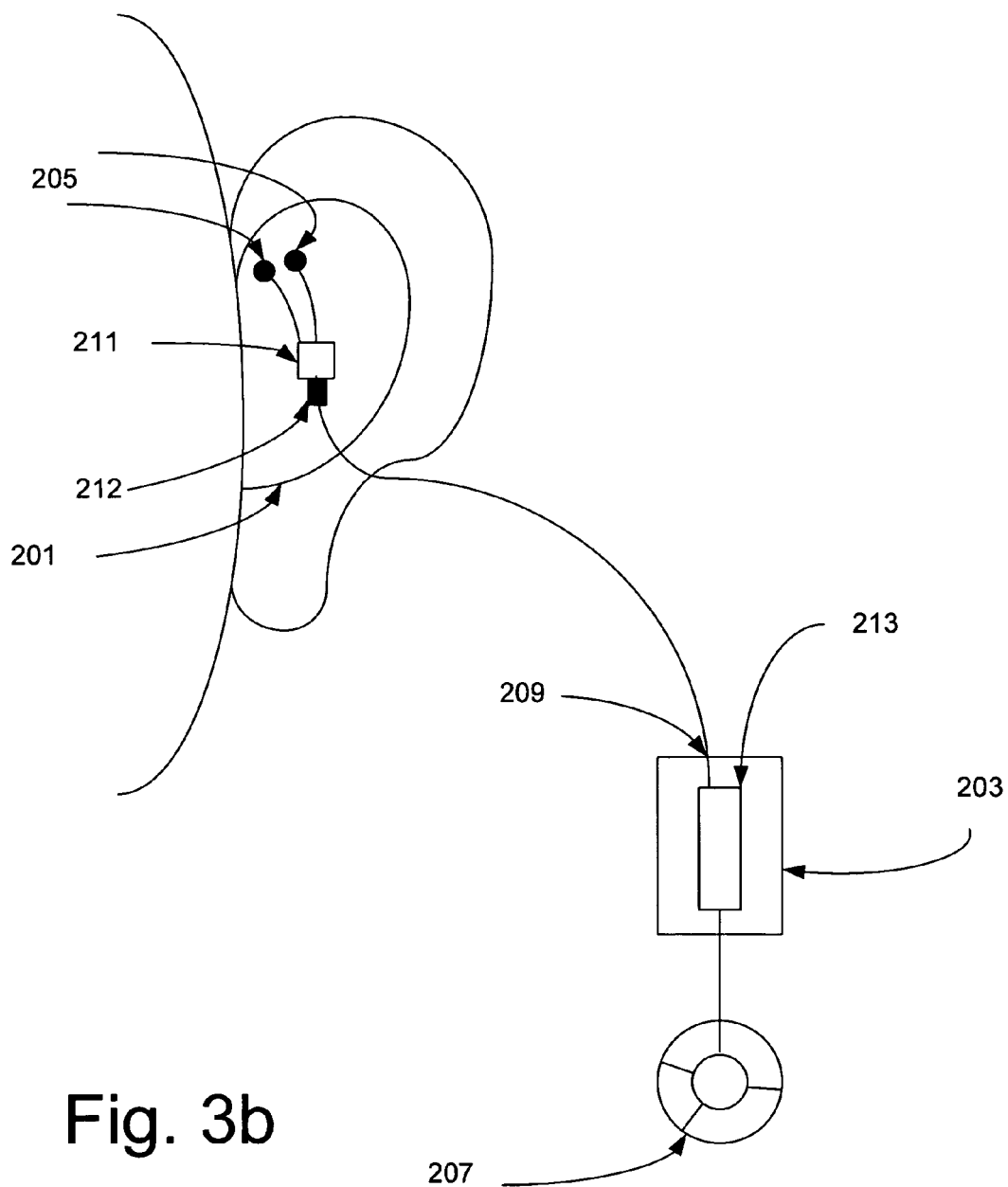
FIG. 3b illustrates another exemplary method of adding an external component that houses a front-end signal processor, to a cochlear implant speech processor, in accordance with an embodiment of the present invention.

FIG. 3b illustrates another exemplary method of adding an external component that houses a front-end signal processor 211, to a cochlear implant signal processor 213, in accordance with an embodiment of the present invention. In an embodiment of the present invention, a hearing aid signal processor 211 and a compatibility matching circuit 212, along with a signal input device 205 such as, for example, microphone(s), direct audio input, or telecoil, housed in an in-the-ear or behind-the-ear hearing aid case 201 may be added to a cochlear implant system with a cochlear implant signal processor 213 housed in a body-worn case 203.

In an embodiment of the present invention, a hearing aid signal processor 211 and a signal input device 205 may be housed in an in-the-ear or behind-the-ear hearing aid case 201. The output of the of the hearing aid signal processor 211 may be fed into a direct audio input/digital input 209 of the cochlear implant signal processor 213, which may be housed in the body-worn case 203.

Figure 3C:
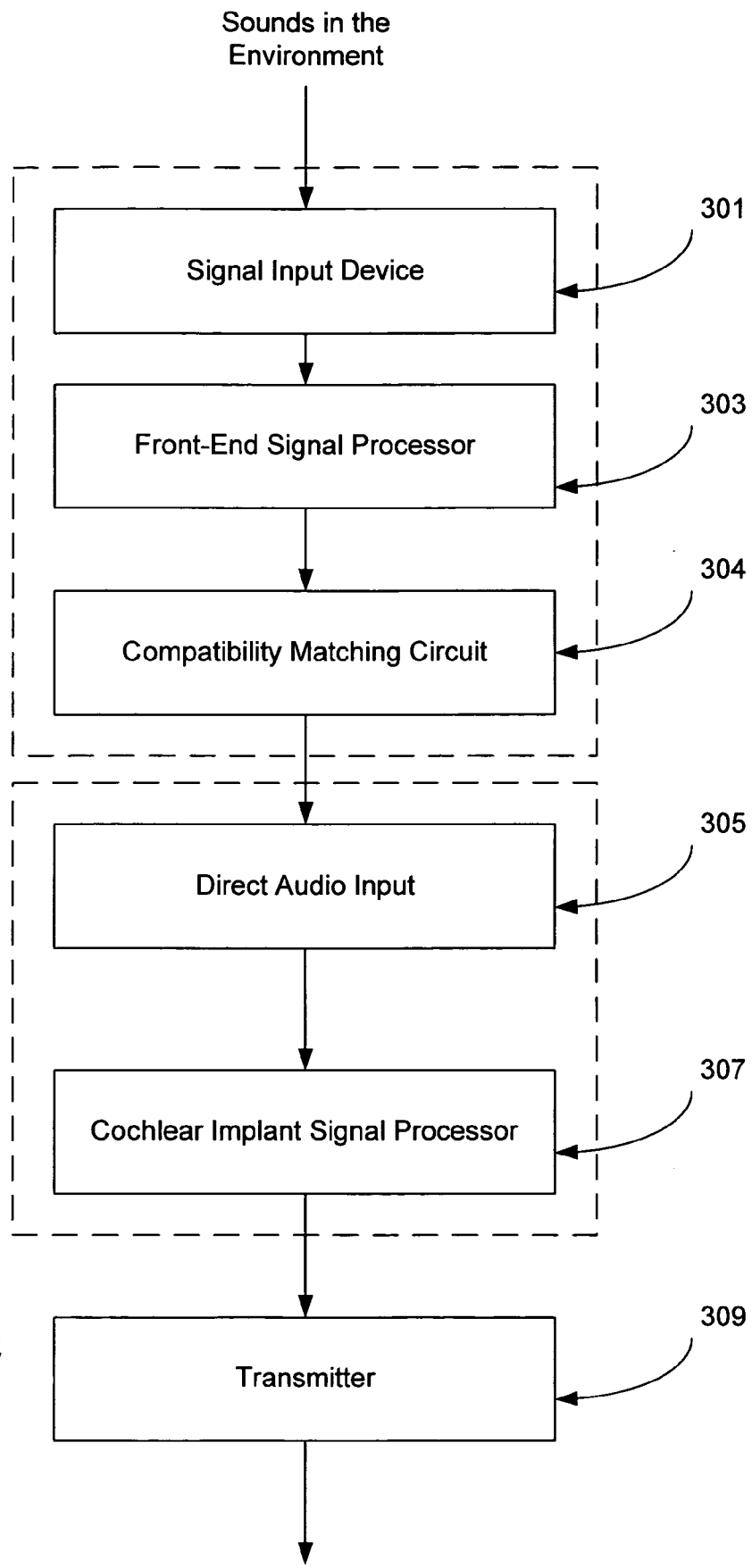
FIG. 3c illustrates a flow diagram of an exemplary signal path of the systems in FIG. 3a and 3b, in accordance with an embodiment of the present invention.

FIG. 3c illustrates a flow diagram of an exemplary signal path of the systems in FIG. 3a and FIG. 3b, in accordance with an embodiment of the present invention. At a first block 301, the sounds in the environment surrounding the user of the hearing aid may be picked up by a signal input device 105 of FIG. 3a in an in-the-ear case such as case 101, a signal input device 205 of FIG. 3b in an in-the-ear or a behind-the-ear case such as case 201. The sounds may be then processed, at a next block 303, by a hearing aid signal processor such as the hearing aid signal processor 111 of FIG. 3a and hearing aid signal processor 211 of FIG. 3b. At a next block 305, the preprocessed signal may be fed through a direct audio input/digital input such as the direct audio input/digital input 109 of FIG. 3a and the direct audio input/digital input 209 of FIG. 3b and into a cochlear implant signal processor such as the cochlear implant signal processor 113 of FIG. 3a and the cochlear implant signal processor 213 of FIG. 3b, at a next block 307. The final processed signal may then go to a transmitter of the cochlear implant system such as, for example, the transmitter 107 of FIG. 3a, and the transmitter 207 of FIG. 3b.

Figure 4A:
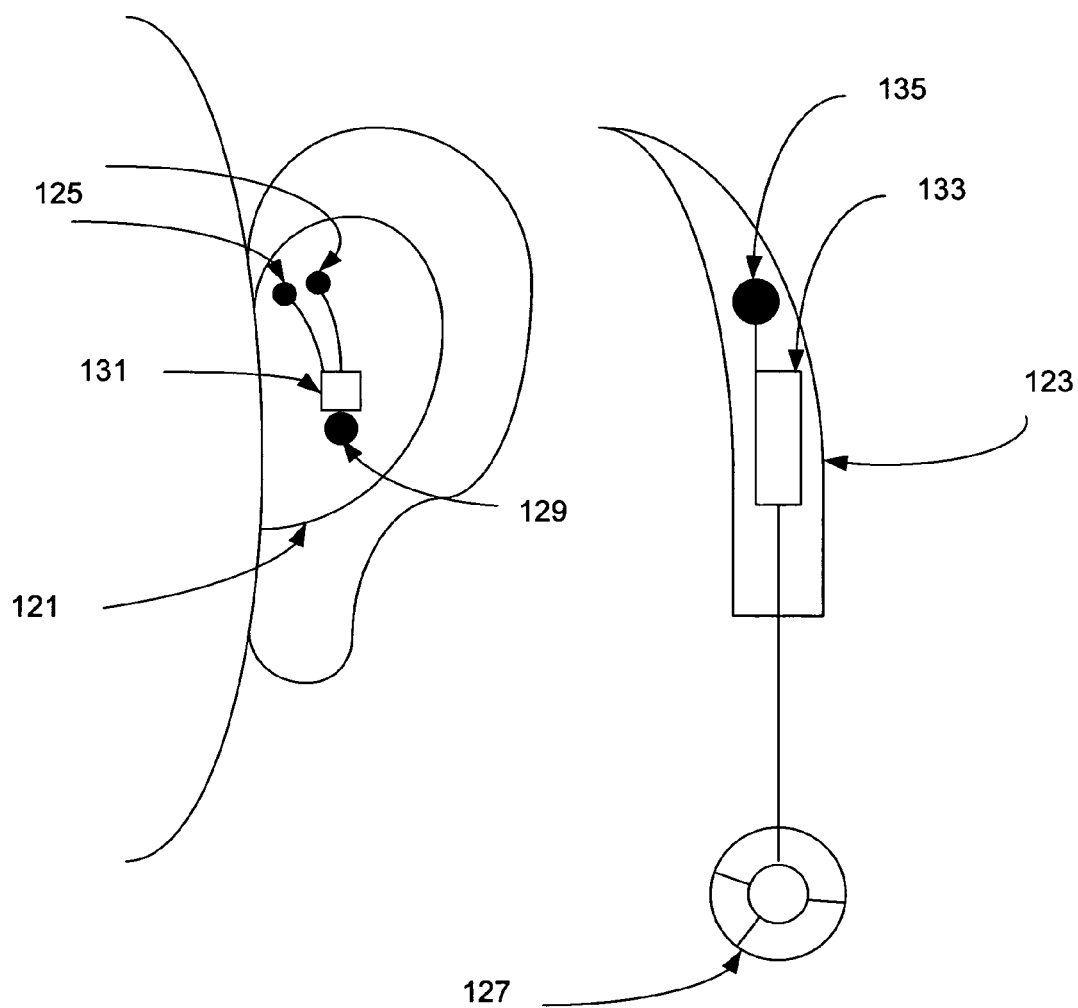
FIG. 4a illustrates an exemplary method of adding an external component that houses a front-end signal processor, to a cochlear implant speech processor, in accordance with an embodiment of the present invention.

FIG. 4a illustrates an exemplary method of adding an external component that houses a front-end signal processor, to a cochlear implant signal processor, in accordance with an embodiment of the present invention. In an embodiment of the present invention, a hearing aid signal processor 131, along with the signal input device 125 such as, for examples, microphone(s), direct audio input, or telecoil, housed in an in-the-ear hearing aid case 121, may be added to a cochlear implant system with a cochlear implant signal processor 133 housed in a behind-the-ear case 123. The signal picked by the signal input device may be processed by the hearing aid signal processor 131 and then transmitted to the cochlear implant in the BTE case 123 via wireless transmission.

In an embodiment of the present invention, an in-the-ear hearing aid case 121 may be used to house the hearing aid signal processor 131, and a behind-the-ear case 123 may house the cochlear implant signal processor 133. The signal may be processed by the hearing aid signal processor 131 and then transmitted to the cochlear implant in the behind-the-ear case 123 via wireless transmission. The wireless transmitter 129 may receive hearing aid processed signal from the hearing aid signal processor 131 and transmit the hearing aid processed signal to the cochlear implant signal processor 133, which may utilize the wireless receiver 135 for receiving the wirelessly transmitted signal. The wireless transmitter 129 connected to the hearing aid signal processor 131 may be used to transmit the hearing aid processed signal to the cochlear implant signal processor 133, which may utilize the wireless receiver 135 for receiving the wirelessly transmitted signal.

Figure 4B:
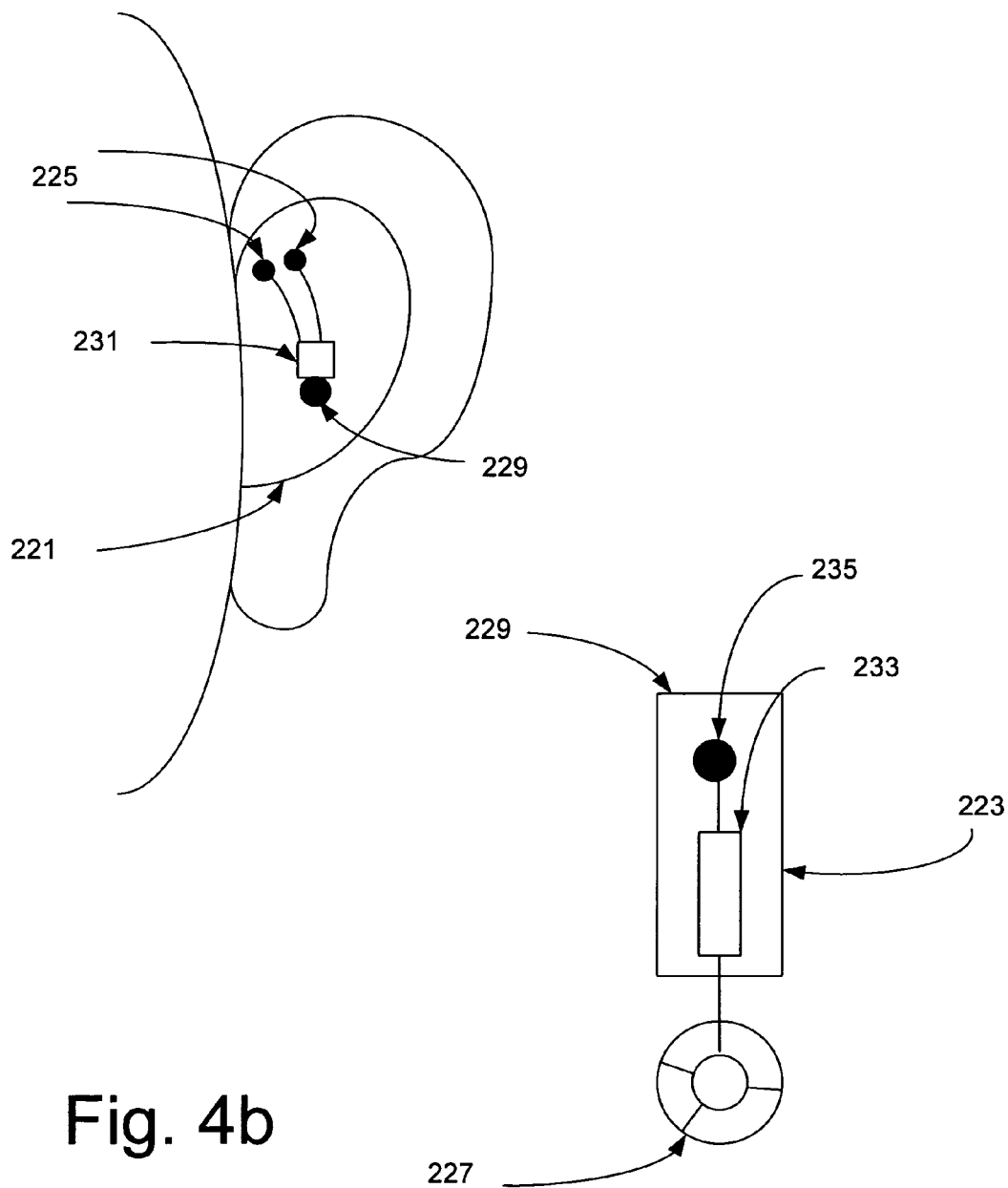
FIG. 4b illustrates another exemplary method of adding an external component that houses a front-end signal processor, to a cochlear implant speech processor, in accordance with an embodiment of the present invention.

FIG. 4b illustrates another exemplary method of adding an external component that houses a front-end signal processor, to a cochlear implant signal processor, in accordance with an embodiment of the present invention. In an embodiment of the present invention, a hearing aid signal processor 231, along with a signal input device 225 such as, for example, microphone(s), direct audio input or telecoil, housed in an in-the-ear or behind-the-ear hearing aid case 221, may be added to a cochlear implant system with a cochlear implant signal processor 233 housed in a body-worn case 223.

In an embodiment of the present invention, an in-the-ear or behind-the-ear hearing aid case 221 may be used to house a hearing aid signal processor 231, and a body-worn case 223 may house the cochlear implant signal processor 233. The signal may be processed by the hearing aid signal processor 231 then transmitted to the cochlear implant in the body-worn case 223 via wireless transmission. The wireless transmitter 229 connected to the hearing aid signal processor 231 may be used to transmit the hearing aid processed signal to the cochlear implant signal processor 233, which may utilize the wireless receiver 235 for receiving the wirelessly transmitted signal.

Figure 4C:
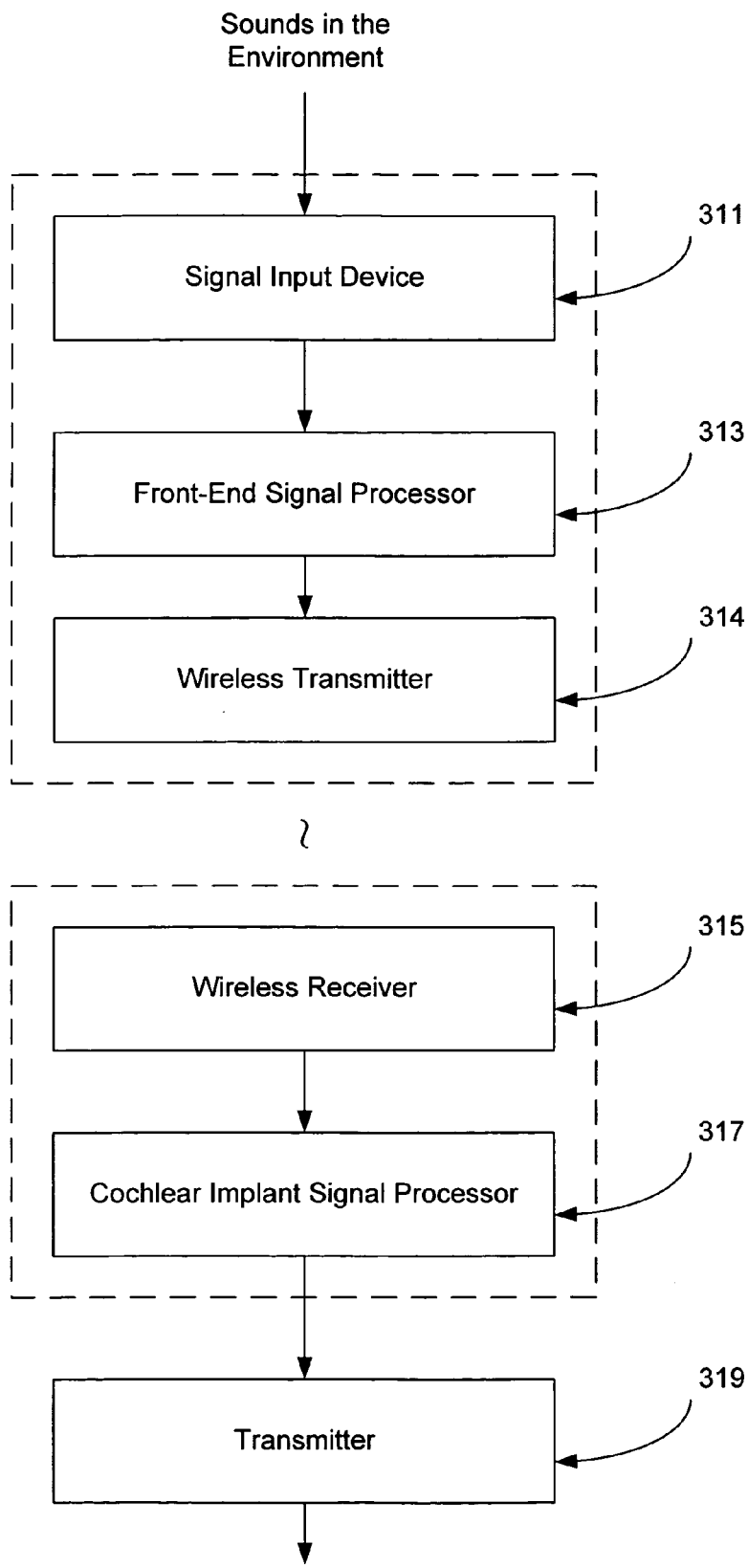
FIG. 4c illustrates a flow diagram of an exemplary signal path of the systems in FIG. 4a and 4b, in accordance with an embodiment of the present invention.

FIG. 4c illustrates a flow diagram of an exemplary signal path of the systems in FIG. 4a and FIG. 4b, in accordance with an embodiment of the present invention. At a first block 311, the sounds in the environment surrounding the user of the hearing aid may be picked up by a signal input device such as, for example, a signal input device 125 of FIG. 4a, in an in-the-ear case such as the in-the-ear case 121 or signal input device 225 of FIG. 4b, in an in-the-ear or behind-the-ear case such as the in-the-ear/behind-the-ear case 223 of FIG. 4b. The sounds may be then processed, at a next block 313, by a hearing aid signal processor such as the hearing aid signal processor 131 of FIG. 4a and the hearing aid signal processor 231 of FIG. 4b. At a next block 314, the preprocessed signal may be transmitted through a wireless transmitter such as the wireless transmitter 129 of FIG. 4a and the wireless transmitter 229 of FIG. 4b. A wireless receiver such as the wireless receiver 135 of FIG. 4a and the wireless receiver 235 of FIG. 4b may then receive the wirelessly transmitted signal at a next block 315. The received preprocessed signal may be fed into a cochlear implant signal processor such as the cochlear implant signal processor 133 of FIG. 4a and the cochlear implant signal processor 233 of FIG. 4b, at a next block 317. The final processed signal may then go to a transmitter of the cochlear implant system such as, for example, the transmitter 127 of FIG. 4a, and the transmitter 227 of FIG. 4b.

In an embodiment of the present invention, such a method of addition of an external component that houses the front-end signal processor, to a cochlear implant signal processor, enables normal procedures to be used to program the front-end signal processor and the cochlear implant signal processor as if they function independently.

Figure 5:
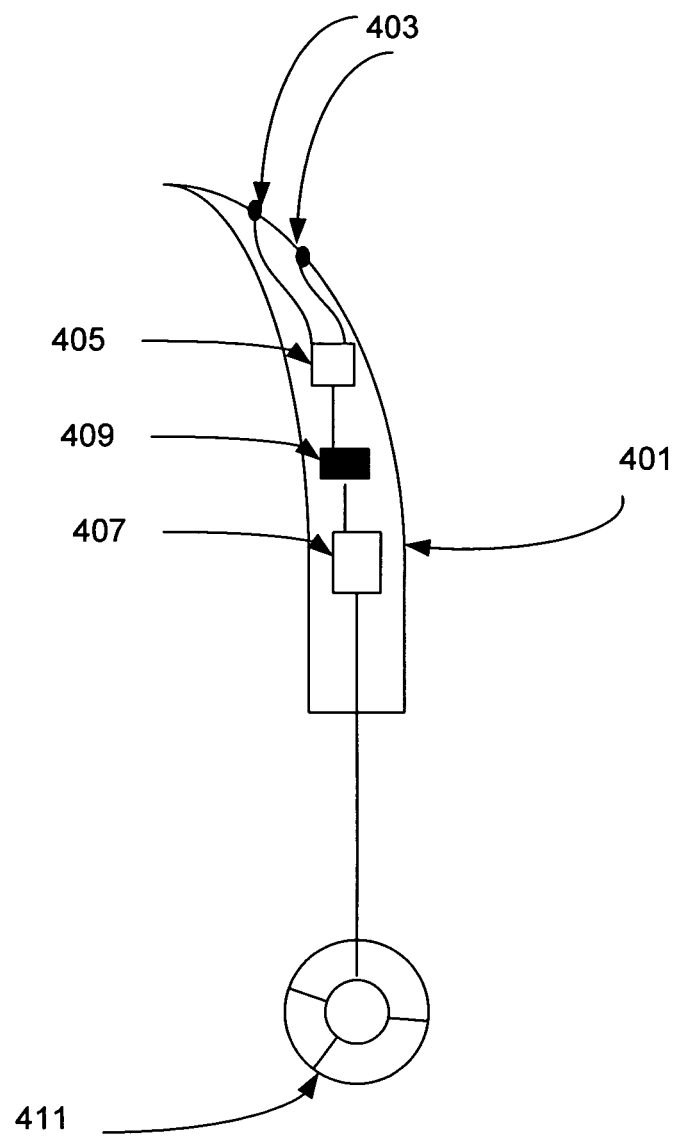
FIG. 5 illustrates an exemplary method of integrating a front-end signal processor, or part(s) of it, into existing components of a cochlear implant system, in accordance with an embodiment of the present invention.

FIG. 5 illustrates an exemplary method of integrating a front-end signal processor, or part(s) of it, into existing components of a cochlear implant system, in accordance with an embodiment of the present invention. In an embodiment of the present invention, a hearing aid signal processor 405 may be integrated into a cochlear implant system with a cochlear implant signal processor 407 housed in a cochlear implant case 401. In another embodiment of the present invention, a compatibility matching circuit 409 may be also integrated into the system.

In an embodiment of the present invention, the signal input device 403 such as, for examples, microphone(s), direct audio input or telecoil, may be a part of the hearing aid signal processor 405. In another embodiment of the present invention, the signal input device 403 may be a part of the cochlear implant system.

In an embodiment of the present invention, a compatibility matching circuit/algorithm 409 may be added to minimize distortion and to eliminate any possible incompatibility such as, for example, signal format, signal scaling and impedance mismatch, etc., between the hearing aid signal processor 405 and the cochlear implant signal processor 407.

Figure 6:
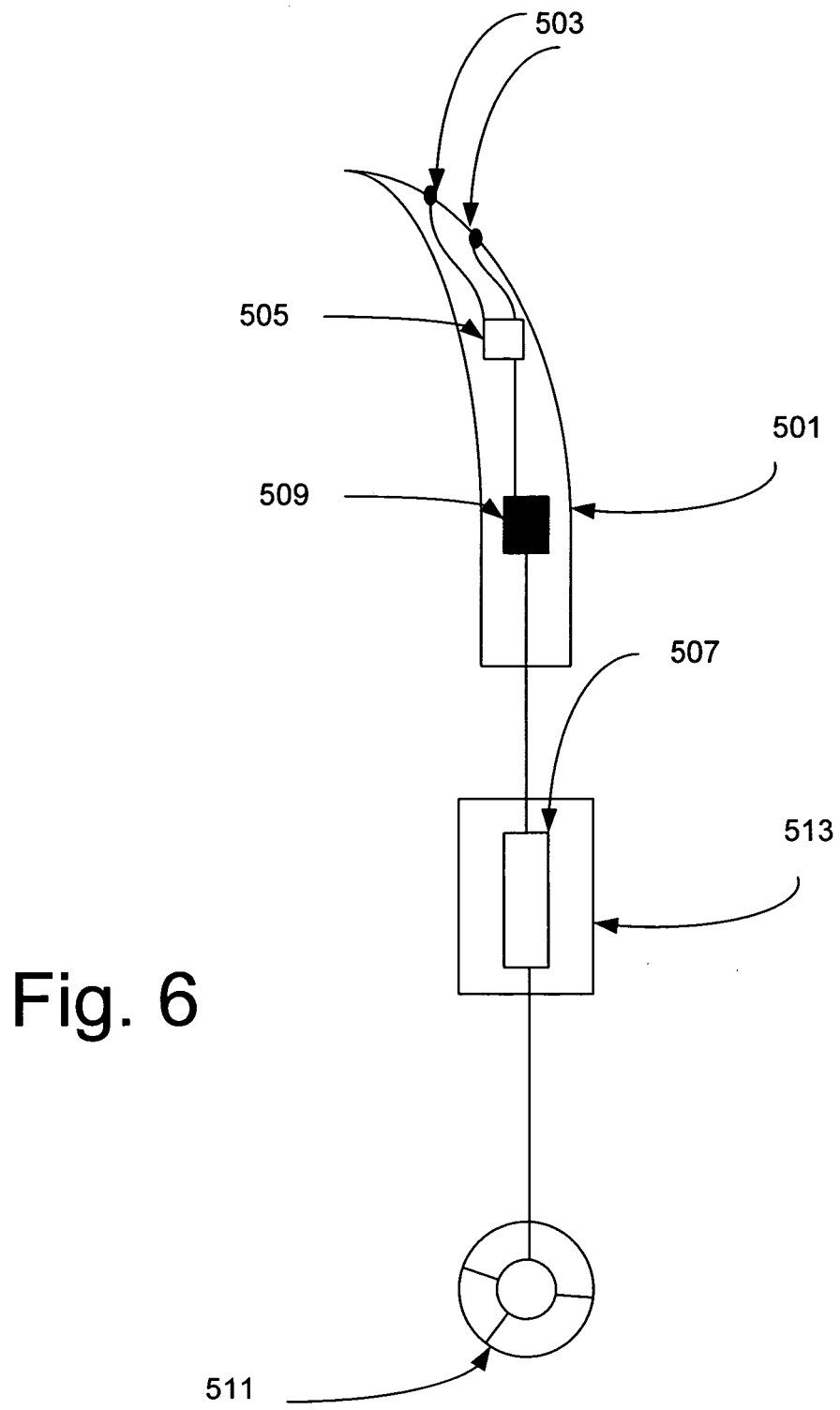
FIG. 6 illustrates an exemplary method of integrating a front-end signal processor, or part(s), of it into existing components of a cochlear implant system, in accordance with an embodiment of the present invention.

FIG. 6 illustrates another exemplary method of integrating a front-end signal processor, or part(s) of it, into existing components of a cochlear implant system, in accordance with an embodiment of the present invention. In an embodiment of the present invention, a hearing aid signal processor 505, housed in a hearing aid case 501, may be integrated into a cochlear implant system, with a cochlear implant signal processor 507 in a cochlear implant case 513. In another embodiment of the present invention, a compatibility matching circuit 509 may be also integrated into the system.

In an embodiment of the present invention, the signal input device 503 such as, for examples, microphones, direct audio input or telecoil, may be a part of the hearing aid signal processor 505. In another embodiment of the present invention, the signal input device 503 may be a part of the cochlear implant system.

In an embodiment of the present invention, the connections to and from the hearing aid signal processor 505 may be in analog or digital format depending on the combination of hearing aid signal processor 505 and cochlear implant signal processor 507. A compatibility matching circuit/algorithm 509 may be added at the interface of the hearing aid signal processor 505 and the cochlear implant signal processor 507.

Figure 7:
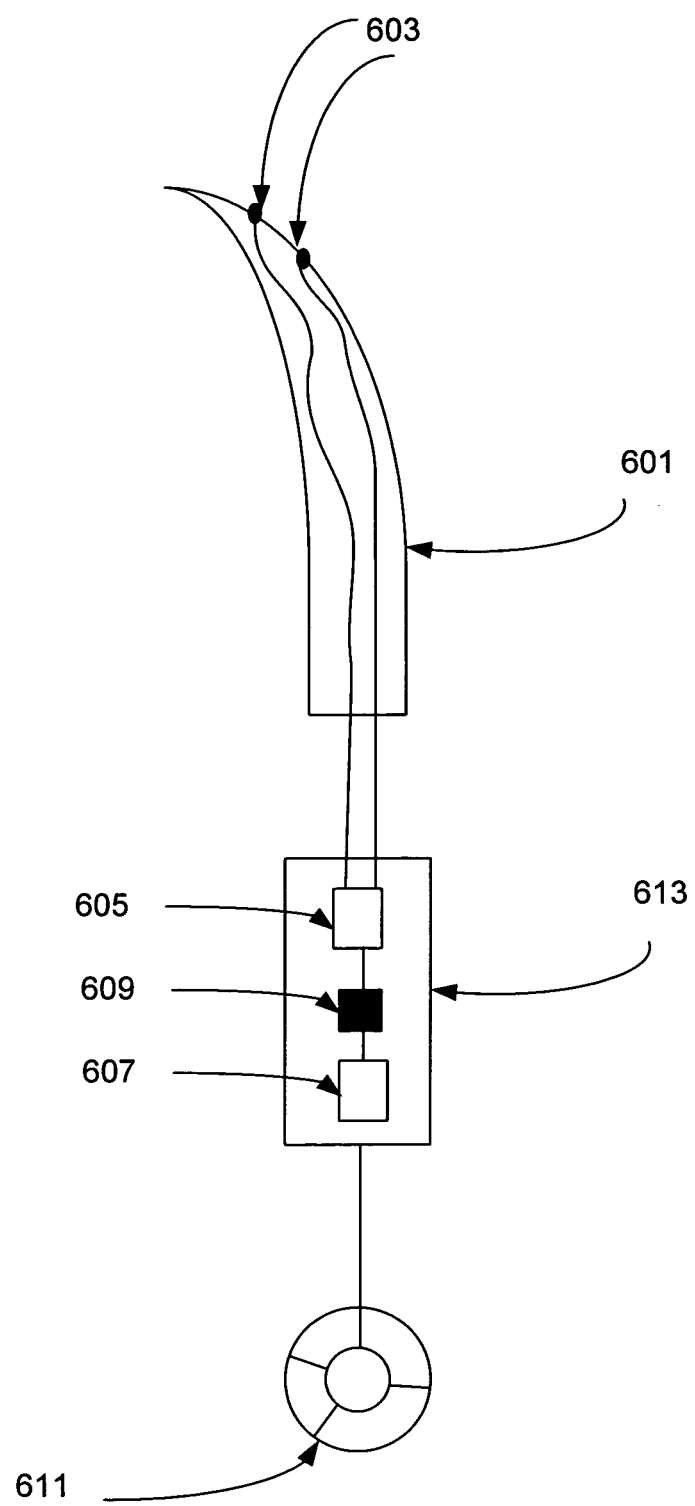
FIG. 7 illustrates another exemplary method of integrating a front-end signal processor, or part(s) of it, into existing components of a cochlear implant system, in accordance with an embodiment of the present invention.

FIG. 7 illustrates another exemplary method of integrating a front-end signal processor, or part(s) of it, into existing components of a cochlear implant system, in accordance with an embodiment of the present invention. In an embodiment of the present invention, a hearing aid signal processor 605 may be integrated into a cochlear implant system with a cochlear implant signal processor 607 housed in a cochlear implant case 613. In another embodiment of the present invention, a compatibility matching circuit/algorithm 609 may be added at the interface of the hearing aid signal processor 605 and the cochlear implant signal processor 607.

In an embodiment of the present invention, the signal input device 603 such as, for examples, microphone(s), direct audio input or telecoil may be a part of the hearing aid signal processor 605. In another embodiment of the present invention, the signal input device 603 may be a part of the cochlear implant system.

Figure 8:
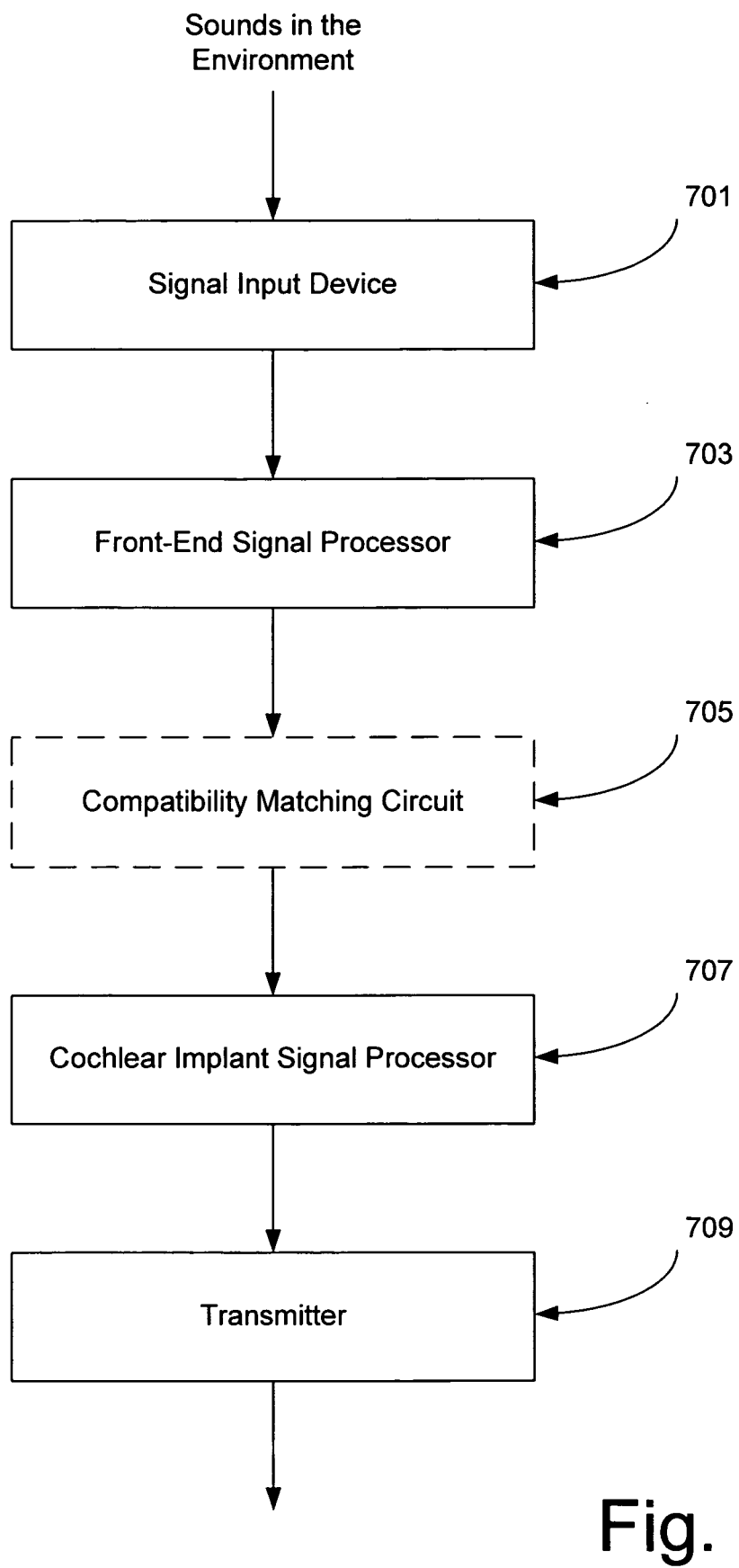
FIG. 8 illustrates flow diagram of an exemplary signal path of the systems in FIG. 5, FIG. 6 and FIG. 7, in accordance with an embodiment of the present invention.

FIG. 8 illustrates a flow diagram of an exemplary signal path of the systems in FIG. 5, FIG. 6 and FIG. 7, in accordance with an embodiment of the present invention. At a first block 701, a signal input device such as, for example, the signal input device of 403 of FIG. 5, the signal input device 503 of FIG. 6, and the signal input device of 603 of FIG. 7 may pick up the sounds from the environment. A front-end signal processor such as the hearing aid signal processor 405 of FIG. 5, the hearing aid signal processor 505 of FIG. 6, and the hearing aid signal processor 605 of FIG. 7, at a next block 703, may pre-process the sounds. In an embodiment of the present invention, at a next block 705, the preprocessed signal may be fed into a cochlear implant signal processor such as the cochlear implant signal processor 407 of FIG. 5, the cochlear implant signal processor of 507 of FIG. 6, and the cochlear implant signal processor 607 of FIG. 7, through a compatibility matching circuit such as the compatibility matching circuit 469 of FIG. 5, the compatibility matching circuit 509 of FIG. 6, and the compatibility matching circuit 609 of FIG. 7. The signal may then get processed by the cochlear implant signal processor at a block 707, and may then be fed to a transmitter of the cochlear implant system such as, for example, transmitter 411 of FIG. 5, transmitter 511 of FIG. 6, or transmitter 611 of FIG. 7, at a block 709.

In an embodiment of the present invention, a front-end processor may be inserted into multiple signal processing stages of a cochlear implant signal processor with the front-end processor being either an integrated part of the cochlear implant signal processor or a functionally distinctive part for bilateral cochlear implants. In an embodiment of the present invention, the front-end processor may receive signals from two different signal input devices. The two different input devices may represent microphone inputs placed in or near the two ears for bilateral cochlear implants. A signal preprocessed by the front-end processor may be fed into two signal processors via a "Y" connection for the bilateral cochlear implants.

Figure 9A:
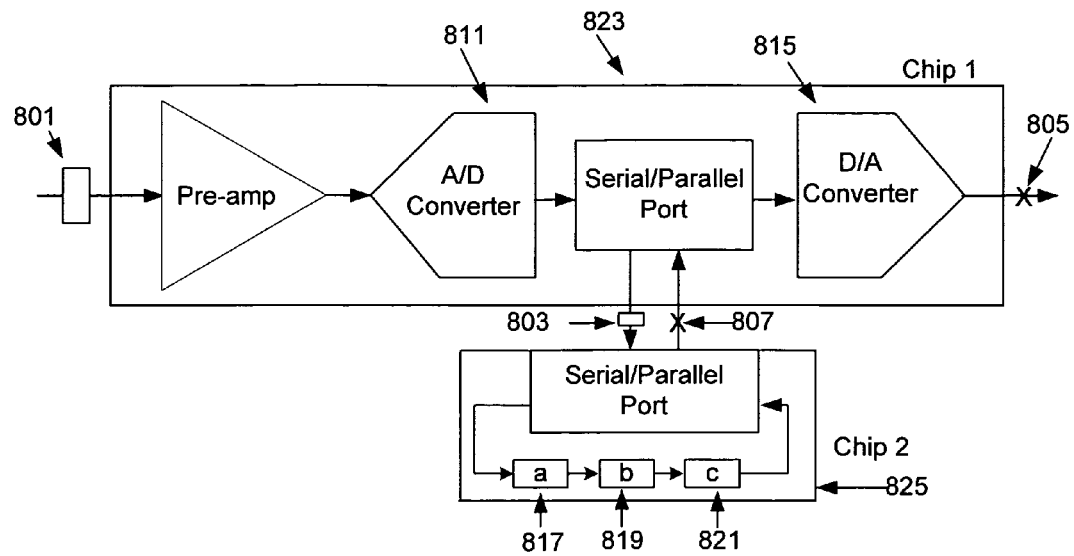
FIG. 9a illustrates an exemplary configuration of a common hearing aid signal processor with multiple signal feeding and extraction points, in accordance with an embodiment of the present invention.

FIG. 9a illustrates an exemplary configuration of a common hearing aid signal processor with multiple signal feeding and extraction points, in accordance with an embodiment of the present invention. In an embodiment of the present invention, the hearing aid signal processor may have multiple signal processing stages such as, for example, stages 817, 819, and 821, and/or multiples components such as, for example, component 823 and component 825. The configuration may have a signal feeding point 801 at one end, and a signal extraction point 805 at the other end. In addition, signals may be fed into and extracted from points other than the two ends, such as signal feeding point 803 and signal extraction point 807. Depending on the functionality needed for the preprocessing of the signal, connections may be made to any of these points, given that signal compatibility issues can be resolved. Multiple feeding and extraction points may provide additional flexibility of utilizing all or part of the functionality of a hearing aid signal processor.

In an embodiment of the present invention, when a hearing aid signal processor may be connected to a cochlear implant signal processor, there may be redundant components such as, for example, the digital-to-analog converter 815 at the output of the hearing aid signal processor and an analog-to-digital converter at the input of a cochlear implant signal processor. In an embodiment of the present invention, a digital connection may be made between the two processors, with a compatibility matching digital interface, to bypass the digital-to-analog converter 815 at the output of the hearing aid signal processor and the analog-to-digital converter at the input of the cochlear implant signal processor to shorten the signal path and to reduce noises introduced by multiple conversions.

Figure 9B:
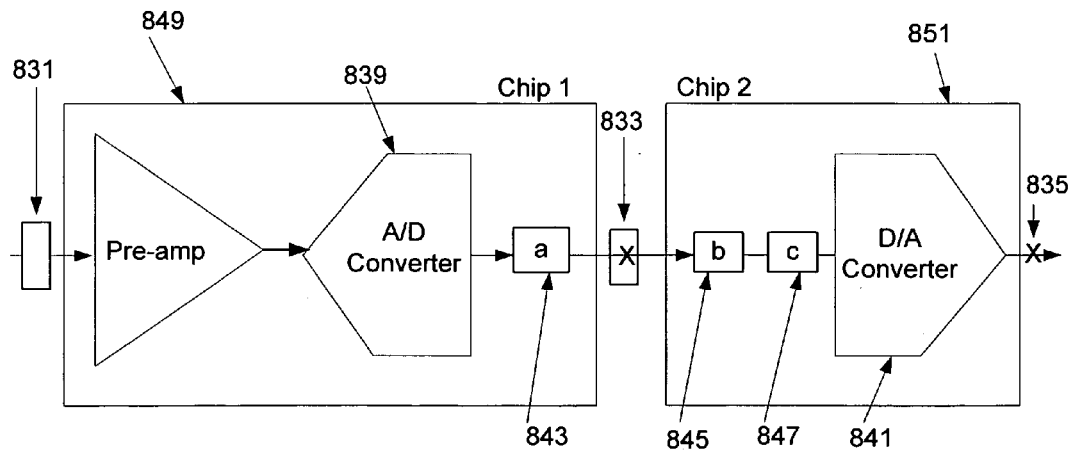
FIG. 9b illustrates another exemplary configuration of a common hearing aid signal processor with multiple signal feeding and extraction points, in accordance with an embodiment of the present invention.

FIG. 9b illustrates another exemplary configuration of a common hearing aid signal processor with multiple signal feeding and extraction points, in accordance with an embodiment of the present invention. In an embodiment of the present invention, the hearing aid signal processor may have multiple signal processing stages such as, for example, stages 843, 845, and 847, and/or multiples components such as, for example, component 849 and component 851. The configuration may have a signal feeding point 831 at one end, and a signal extraction point 835 at the other end. In addition, signals may be fed into and extracted from points other than the two ends, such as signal feeding and/or extraction point 833. Depending on the functionality needed for the preprocessing of the signal, connections may be made to any of these points, given that signal compatibility issues can be resolved. Multiple feeding and extraction points may provide additional flexibility of utilizing all or part of the functionality of a hearing aid signal processor.

In an embodiment of the present invention, when a hearing aid signal processor may be connected to a cochlear implant speech processor, there may be redundant components such as, for example, the digital-to-analog converter 841 at the output of the hearing aid signal processor and an analog-to-digital converter at the input of a cochlear implant signal processor. In an embodiment of the present invention, a digital connection may be made between the two processors, with a compatibility matching digital interface, to bypass the digital-to-analog converter 841 at the output of the hearing aid signal processor and the analog-to-digital converter at the input of the cochlear implant signal processor to shorten the signal path and to reduce noises introduced by multiple conversions.

Figure 10:
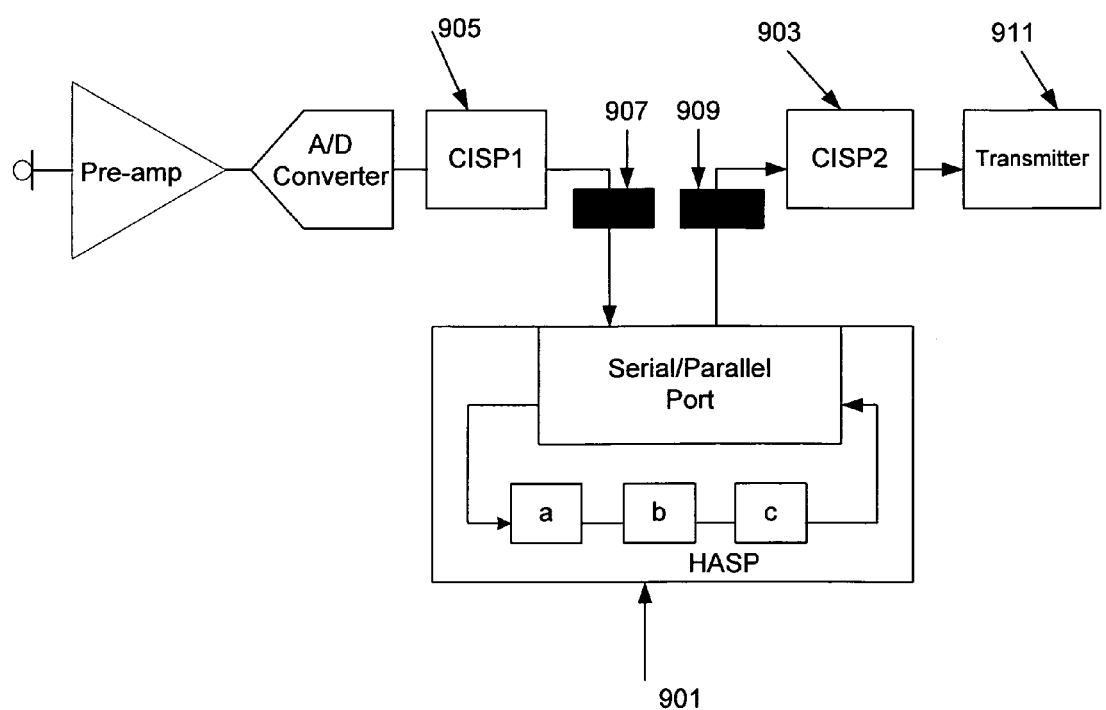
FIG. 10 illustrates an exemplary method of integrating a hearing aid signal processor with a cochlear implant signal processor that has multiple signal processing stages and/or multiple components, in accordance with an embodiment of the present invention.

FIG. 10 illustrates an exemplary method of integrating a hearing aid signal processor 901 with a cochlear implant speech processor 903 and 905, in accordance with an embodiment of the present invention. The cochlear implant system may have multiple signal processing stages and/or multiple components. In an embodiment of the present invention, the hearing aid signal processor 901 may be integrated into the cochlear implant system in a "sandwich" fashion. In an embodiment of the present invention, the integrated system may also have two compatibility matching circuits 907 and 909. The compatibility matching circuit 907 may be added between the hearing aid signal processor 901 and the cochlear implant signal processor 905. The compatibility matching circuit 909 may be added between the hearing aid signal processor 901 and the cochlear implant signal processor 903.

In an embodiment of the present invention, while both the hearing aid signal processor 901 and the cochlear implant signal processor 903 and 905 may be programmed utilizing separate programming leads, or a single piece of software may be used to program both processors to allow the user to see the overall effect of the programming.

It should be clear that the signals in any embodiment of the present invention may be in digital format and/or in analog format as required by the design of the embodiment. It should also be clear that the processing done by the processors of the system may comprise processing by hardware, software, or a combination thereof. It should be also understood that wireless transmission may replace wired connections as deemed appropriate in any embodiment of the present invention.

While the present invention has been described with reference to certain embodiments, it will be understood by those skilled in the art that various changes may be made and equivalents may be substituted without departing from the scope of the present invention. In addition, many modifications may be made to adapt a particular situation or material to the teachings of the present invention without departing from its scope. Therefore, it is intended that the present invention not be limited to the particular embodiment disclosed, but that the present invention will include all embodiments falling within the scope of the appended claims.

What is claimed is:

1. A system that enhances the performance of an existing cochlear implant using a hearing aid preprocessing device, the system comprising:
    said hearing aid preprocessing device comprising:
        a plurality of hearing aid signal input devices, comprising one or both of a hearing aid microphone and a hearing aid telecoil,
        a first processor coupled to said plurality of hearing aid signal input devices for performing signal processing on signals received from said plurality of hearing aid signal input devices; and said existing cochlear implant comprising:
    at least one cochlear implant signal input device, comprising one or both of a cochlear implant direct audio input and a wireless receiver for receiving said processed signals from said hearing aid preprocessing device;
        a second processor that processes and encodes said signals received by said at least one cochlear implant signal input device,
        a transmitter for transmitting said processed and encoded signals to an implanted portion of said existing cochlear implant;
    wherein said existing cochlear implant is retrofitted with said hearing aid preprocessing device by communicatively coupling an output of said hearing aid preprocessing device with one or both of said at least one cochlear implant signal input device of said existing cochlear implant, and
    wherein said hearing aid preprocessing device comprises a compatibility matching circuit coupled to said first processor for adjusting the processed signals received from said first processor to match at least one signal requirement of said existing cochlear implant.

2. The system according to claim 1 wherein said at least one signal requirement of said existing cochlear implant corresponds to a signal format requirement.

3. The system according to claim 1 wherein said at least one signal requirement of said existing cochlear implant corresponds to a signal scaling requirement.

4. The system according to claim 1 wherein said at least one signal requirement of said existing cochlear implant corresponds to an impedance matching requirement.

5. The system according to claim 1 wherein said compatibility matching circuit is configured to minimize distortion of said processed signals received from said first processor of said hearing aid preprocessing device.

* * * * *